United States Patent
Tanaka et al.

(10) Patent No.: US 9,580,747 B2
(45) Date of Patent: *Feb. 28, 2017

(54) DNA CHIP WITH MICRO-CHANNEL FOR DNA ANALYSIS

(71) Applicants: Panasonic Corporation, Osaka (JP); IMEC vzw, Leuven (BE)

(72) Inventors: Hiroyuki Tanaka, Nara (JP); Benjamin Jones, Leuven (BE); Paolo Fiorini, Leuven (BE)

(73) Assignees: PANASONIC CORPORATION, Osaka (JP); IMEC VZW, Leuven (BE)

( * ) Notice: Subject to any disclaimer, the term of this patent is extended or adjusted under 35 U.S.C. 154(b) by 171 days.

This patent is subject to a terminal disclaimer.

(21) Appl. No.: 14/196,332

(22) Filed: Mar. 4, 2014

(65) Prior Publication Data

US 2014/0186936 A1    Jul. 3, 2014

Related U.S. Application Data

(63) Continuation of application No. PCT/JP2013/062307, filed on Apr. 19, 2013.

(30) Foreign Application Priority Data

Apr. 20, 2012    (JP) ................... 2012-096893

(51) Int. Cl.
*C12Q 1/68* (2006.01)
*B01L 7/00* (2006.01)
*B01L 3/00* (2006.01)

(52) U.S. Cl.
CPC ........ *C12Q 1/686* (2013.01); *B01L 3/502707* (2013.01); *B01L 7/52* (2013.01);
(Continued)

(58) Field of Classification Search
CPC .............. C12Q 1/686; C12Q 2565/629; B01L 2300/0816; B01L 2300/0861;
(Continued)

(56) References Cited

U.S. PATENT DOCUMENTS 7,807,360 B2    10/2010 Kim et al.
2008/0112854 A1*  5/2008 Park .................. B01L 3/502707
                                                            422/400

(Continued)

FOREIGN PATENT DOCUMENTS

JP    2007-175006    7/2007
JP    2011-522219    7/2011

OTHER PUBLICATIONS

International Search Report issued Aug. 6, 2013 in International (PCT) Application No. PCT/JP2013/062307.
(Continued)

*Primary Examiner* — Gautam Prakash
(74) *Attorney, Agent, or Firm* — Wenderoth, Lind & Ponack, L.L.P.

(57) ABSTRACT

A DNA chip with micro-channel for DNA analysis of DNA included in an analyte according to a PCR method is a DNA chip with micro-channel for DNA analysis in which is silicon (first layer) and plastic (second layer) are laminated, wherein the second layer is formed on a partial area of the first layer, and the second layer includes: a reagent; a liquid transporting system; and a sensor, and the first layer includes a PCR reactor provided on an area on which the second layer is not formed.

2 Claims, 7 Drawing Sheets

(52) U.S. Cl.
CPC ............... *B01L 2300/0816* (2013.01); *B01L 2300/0861* (2013.01); *B01L 2300/0887* (2013.01); *B01L 2300/12* (2013.01); *B01L 2300/1805* (2013.01); *B01L 2300/1883* (2013.01); *B01L 2400/0439* (2013.01)

(58) Field of Classification Search
CPC ......... B01L 2300/0887; B01L 2300/12; B01L 2300/1805; B01L 2300/1883; B01L 2400/0439; B01L 3/502707; B01L 7/52
USPC ................................ 435/287.1, 287.2, 288.7
See application file for complete search history.

(56) References Cited

U.S. PATENT DOCUMENTS

| | | | |
|---|---|---|---|
| 2009/0023610 A1* | 1/2009 | Peytavi | B01L 3/5027 506/39 |
| 2009/0227476 A1* | 9/2009 | Malcolm | B01L 7/52 506/39 |
| 2009/0269767 A1 | 10/2009 | Soderlund et al. | |

OTHER PUBLICATIONS

M. Palmieri et al., "Advanced Microfluidic Packaging for Molecular Diagnostics", 43$^{rd}$ International Symposium on Microelectronics 2010, (IMAPS 2010), pp. 36-41.

P. F. Man et al., "Microfluidic Plastic Capillaries on Silicon Substrates: A New Inexpensive Technology for Bioanalysis Chips", Micro Electro Mechanical Systems, 1997, MEMS '97, Proceedings, IEEE., Tenth Annual International Workshop on Jan. 26, 1997, pp. 311-316.

I. Yamashita et al., Realizing Rapid On-site SNP Diagnosis, Panasonic Technical Journal, Oct. 15, 2011, col. 57, No. 3, pp. 21-26.

B. Majeed et al., "Silicon Micro-Pillar Filter Fabrication for DNA Separation in Lab-on-Chip System", Electronics Packaging Technology Conference (EPTC), 2012 IEEE 14$^{th}$, Dec. 5, 2012, pp. 52-56.

B. Majeed et al., "Silicon Based System for Single-Nucleotide-Polymorphism Detection: Chip Fabrication and Thermal Characterization of Polymerase Chain Reaction Microchamber", Japanese Journal of Applied Physics, Apr. 20, 2012, vol. 51, 04DL01 (9 pages).

English translation of the International Preliminary Report on Patentability and Written Opinion dated Oct. 21, 2014.

Extended European Search Report dated Oct. 15, 2015, issued in European Patent Application No. 13778499.7.

Sauer-Budge et al., "Low cost and manufacturable complete microTAS for detecting bacteria", Lab on a Chip, 2009, vol. 9, No. 19, pp. 2803-2810.

* cited by examiner

DNA CHIP WITH MICRO-CHANNEL FOR DNA ANALYSIS

CROSS-REFERENCE TO RELATED APPLICATIONS

This is a continuation application of International Application No. PCT/JP2013/062307, with an international filing date of Apr. 19, 2013, which claims priority of Japanese Patent Application No. 2012-96893 filed on Apr. 20, 2012, the contents of which is incorporated herein by reference.

BACKGROUND

1. Technical Field

The present disclosure relates to a chip with micro-channel which is formed on a laminated substrate of silicon and plastic. More particularly, the present disclosure relates to a chip with micro-channel which integrally has functionalities for quickly and conveniently extracting and amplifying desired DNA from an analyte containing a gene, or detecting a sequence of the DNA.

2. Related Art

In recent years, progress of genetic diversity analysis and expression analysis has been outstanding owing to improvement of DNA analysis techniques. Particularly in medical fields, the relationship between diseases and genes attracts attention. For example, by analyzing information of individual genetic information (specific DNA sequence) related to a disease, suitable treatment or administration can be carried out for each individual patient (personalized medicine). In personalized medicine, in situ diagnostics are most desirable, and speedy and convenient techniques with a strong aspect of POCT (Point of Care Testing) are desired. Therefore, it is strongly desired to realize a device capable of quickly and conveniently extracting and amplifying DNA of a gene to be analyzed from a collected analyte such as blood, and detecting a sequence of the DNA.

As one of means to meet these requirements, micro-total analysis systems (μTAS) (also called as a lab-on-chip) have attracted attention in recent years. In the μTAS or lab-on-chip, micro-channels and ports having fine structures in a micro-meter order are provided in a substrate, and various kinds of operations including mixing, extraction, refinement, chemical reaction and/or analysis of a substance, and so on can be performed within the structures. The μTAS has been partially put into practical use. Since various kinds of operations are performed within fine structures, the μTAS has the following features compared to the same type of device in common size: (1) the use amounts of a sample and a reagent are remarkably small; (2) the analysis time is short; (3) the sensitivity is high; (4) it can be carried to an actual spot to perform analysis on the spot; and (5) it is disposable. Structures prepared for the purpose described above and having fine structures such as micro-channels and ports in a substrate are collectively called as a chip with micro-channel or device with micro-fluid.

For analyzing DNA in a gene in an analyte in a short time using a chip with micro-channel, it is necessary to incorporate functionalities of extraction and amplification into the chip, and realization of a fine filter for separating impurities such as blood cells and a PCR (polymerase chain reaction) capable of increasing and decreasing the temperature at a high speed is required. In addition, convenience in use is required, and it is therefore desirable to be able to stably retain an analyte, a reagent and the like in the chip. Further, in personalized medicine applications, it is desirable to have a configuration that allows treatment from blood, and to be able to sense a single base-multiple system (SNP) in DNA at a detection section. That is, it is desired to realize a versatile chip that can flexibly adapt to operating conditions.

However, due to limitations on the nature of a material of a substrate that forms a chip with micro-channel, it is difficult to realize a device with micro-channel which meets all the foregoing requirements. The reason for this will be described below.

Plastic or silicon is used as a material of a substrate of a chip with micro-channel. The plastic substrate has such a feature that material costs are relatively low, it is easy to perform cutting processing, and affinity with a biological/bio material is relatively high, so that a reagent is easily retained, and so on. On the other hand, however, the plastic substrate has the problem that it is not suitable for formation of a fine filter structure for separating impurities such as blood cells and formation of a PCR reactor for which it is required to increase and decrease the temperature at a high speed, such as a PCR (polymerase chain reaction), because it is difficult to process fine structures in a sub-micro-meter order and the thermal conductivity of the material is not satisfactory. The silicon substrate is suitable for formation of a fine filter structure and a PCR reactor because fine structures are easily formed by a semiconductor lithography technique and the thermal conductivity is higher by 2 to 3 order of magnitude than that of plastic. On the other hand, however, there is the problem that the unit price of the material is high in comparison with plastic, and the silicon substrate is not suitable for storage of a reagent because affinity between the surface of silicon and a biological/bio material is not necessarily high, and therefore non-specific adsorption of a protein and DNA occurs. As described above, plastic and silicon have mutually contradictory advantages and disadvantages, and with a configuration using a substrate of only one of silicon and plastic, conditions required for a chip with micro-channel for used in DNA analysis cannot be adequately satisfied.

As means for solving the above-described problems, a chip with micro-channel has been proposed in which a PCR reactor is arranged on a silicon chip, a reagent is stored in a plastic section, and the silicon layer (first layer) and the plastic layer (second layer) are laminated (Proceeding of 43rd International Symposium on Microelectronics (IMAPS2010) 000036).

In Proceeding of 43rd International Symposium on Microelectronics (IMAPS2010) 000036, there is disclosed a chip with micro-channel in which a first layer and a second layer are laminated, wherein the first layer includes a PCR reactor and a sensor, the second layer includes a reagent, and the reagent is supplied to the first layer during operation. Since a PCR reactor is formed on the first layer made of silicon having excellent thermal conductivity, and a reagent is held in the second layer, increasing and decreasing of temperature at a high speed and convenient treatments can be both achieved. In the disclosed method, however, the PCR reactor and the sensor are formed integrally on the first layer, so that a distance between the PCR reactor and the sensor is limited. Therefore, there is the problem that heat is easily transmitted to the sensor section to deteriorate the functionality of the sensor (—particularly when a reagent is held in the sensor section—). Further, there is the problem that restriction arises when a heat exhausting section such as a heat sink is arranged. That is, there is no space to arrange a large-size heat sink, so that heat dissipation during cooling operation of the PCR reactor becomes insufficient, leading to a reduction in temperature increasing and decreasing speed of PCR.

Further, in the disclosed method, only one PCR reactor is mounted, and only a refined genome can be used as an analyte, so that a treatment from blood cannot be performed. The method cannot adapt to applications that require two stages of PCRs: a PCR intended for extracting a genome to be analyzed from blood and a PCR intended for selectively amplifying DNA based on presence/absence of a SNP in the object to be analyzed. When two or more PCR reactors are mounted, the capacity (i.e. size) of the heat sink should be doubled in theory, and therefore the space to arrange the heat sink is limited in the disclosed structure.

That is, the conventional structure has the major problem that for an intended application, arrangement relationship between the PCR reactor and sensor and the place to hold a reagent is not optimum, and therefore the temperature cannot be increased and decreased at a sufficiently high speed.

The present disclosure has been made for solving the above-described problems. One non-limiting and exemplary embodiment provide a DNA chip with micro-channel for DNA analysis, which performs extraction and amplification of DNA or detection of a sequence of the DNA quickly and conveniently, by optimizing the arrangement of a PCR reactor and a sensor and a place to hold a reagent to secure a place where a heat sink having a sufficient size can be arranged, and by enhancing heat dissipation performance to sufficiently improve the temperature increasing and decreasing speed of PCR.

SUMMARY

In one general aspect, the techniques disclosed here feature: a DNA chip with a micro-channel for DNA analysis of DNA included in an analyte according to a PCR method, the DNA chip includes:
 a first layer made of silicon; and
 a second layer made of plastic,
 wherein the second layer is formed on a partial area of the first layer, and
 the second layer includes:
 a liquid transporting system; and
 a sensor,
 the first layer includes a PCR reactor provided on an area on which the second layer is not formed.

In this way, a reagent and a sensor are stored in a plastic section (second layer) having thermal conductivity lower than that of silicon (first layer), so that the problem that heat conduction to the sensor and the reagent easily occurs during operation of a PCR reactor is dissolved. That is, the PCR reactor can be operated without deteriorating the functionality of the sensor.

According to the present disclosure, there can be provided a DNA chip with micro-channel for DNA analysis, which is capable of performing extraction and amplification of DNA or detection of a sequence of the DNA quickly and conveniently, by enhancing heat dissipation performance of PCR to sufficiently improve the temperature increasing and decreasing speed of the PCR.

Additional benefits and advantages of the disclosed embodiments will be apparent from the specification and figures. The benefits and/or advantages may be individually provided by the various embodiments and features of the specification and drawings disclosure, and need not all be provided in order to obtain one or more of the same.

BRIEF DESCRIPTION OF THE DRAWINGS

The present disclosure will become readily understood from the following description of non-limiting and exemplary embodiments thereof made with reference to the accompanying drawings, in which like parts are designated by like reference numeral and in which.

DETAILED DESCRIPTION

According to a first aspect of the present disclosure, a DNA chip with a micro-channel for DNA analysis of DNA included in an analyte according to a PCR method, the DNA chip includes:
 a first layer made of silicon; and
 a second layer made of plastic,
 wherein the second layer is formed on a partial area of the first layer, and
 the second layer includes:
 a liquid transporting system; and
 a sensor, and
 the first layer includes a PCR reactor provided on an area on which the second layer is not formed.

Further, as a DNA chip of a second aspect, in the first aspect, wherein the PCR reactor may be provided on an area closer to an end of the first layer than to the center of the first layer.

In this way, the PCR reactor is arranged on the outer peripheral area of the chip, and positioned away from the sensor section, so that a large-size heat sink having a sufficient cooling capacity can be arranged. That is, heat dissipation during cooling operation of the PCR reactor can be made sufficient, so that the temperature increasing and decreasing speed of PCR can be enhanced.

Further, as a DNA chip of a third aspect, in the second aspect, wherein at least two PCR reactors may be provided on the first layer,
 the at least two PCR reactors may be connected each other.

In this way, the DNA chip with micro-channel for DNA analysis can also be used in applications requiring two stages of PCR, i.e. applications of PCR from blood, SNP analysis and so on, and also in this case, a large-size heat sink having a sufficient cooling capacity can be arranged. That is, even in a system having two or more PCR reactors, heat dissipation during cooling operation of PCR reactors can be made sufficient, so that the temperature increasing and decreasing speed of PCR can be enhanced.

EMBODIMENT 1

Embodiments of the present disclosure will be described below with reference to the drawings.

Figure 1:
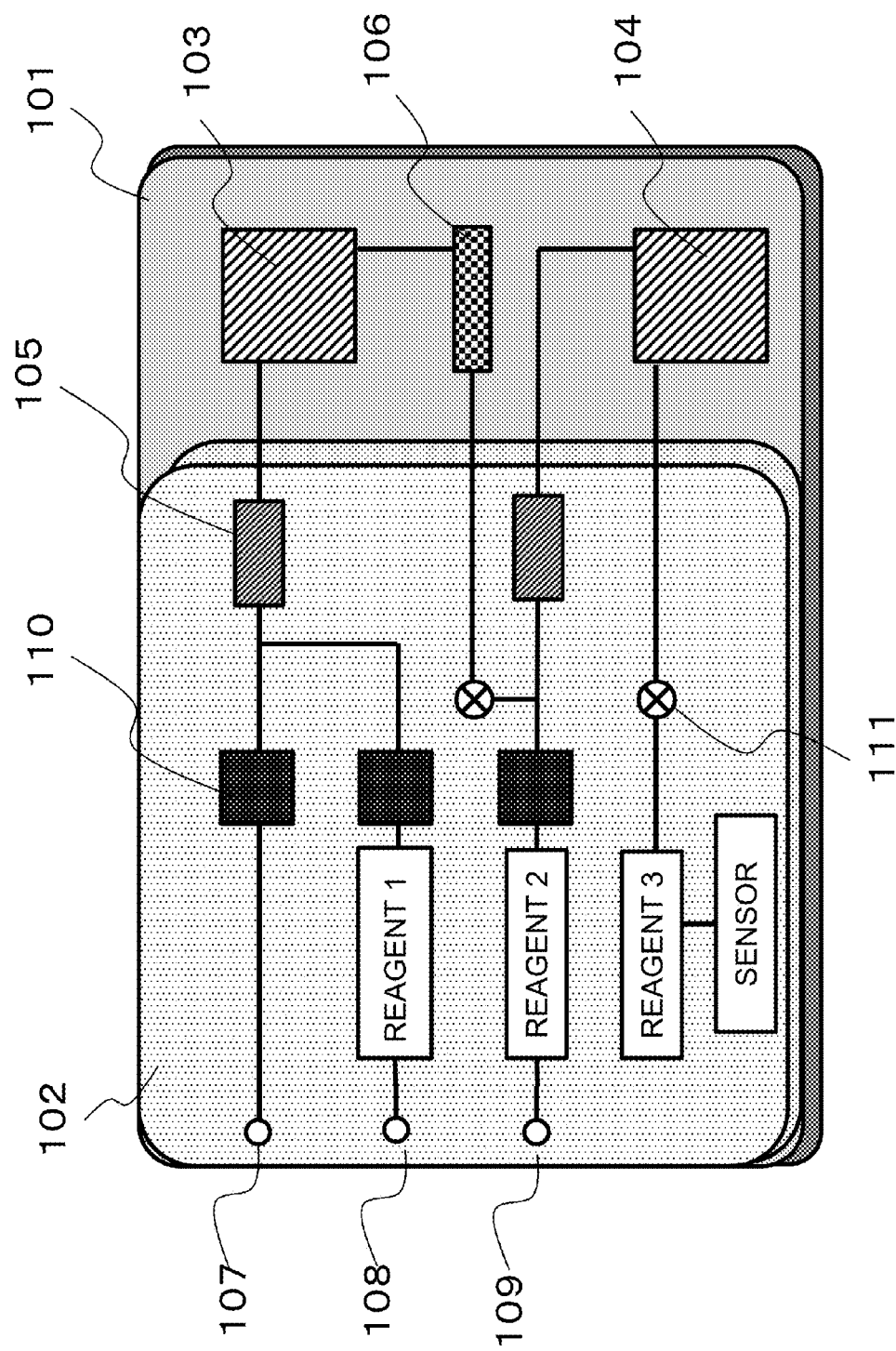
FIG. 1 is a conceptual view of a DNA chip with micro-channel for DNA analysis according to the present disclosure.

FIG. 1 is a conceptual view of a DNA chip with micro-channel for DNA analysis according to the present disclosure. A chip A: 101 is made of silicon (hereinafter, referred to as a first layer), and as a section made to serve as a common platform, a PCR reactor (1) 103 and a PCR reactor (2) 104, and also a mixer 105 and a micro-sieve 106 are connected as in the figure. The PCR reactors (1) 103 and (2) 104 are arranged on an area closer to the end of the first layer than the center of the first layer.

A chip B: 102 is made of plastic (hereinafter, referred to as a second layer), for example, PMMA (polymethylmethacrylate resin) or PDMS (polydimethylsiloxane) may be used. Further, an adhesive or elastomer may be used for the connection section with the first layer, and the second layer is connected so as not to overlap the PCR reactors (1) 103 and (2) 104 of the first layer. As the reagent, reagents (1) and (2) such as a primer and polymerase which are used for reaction in the PCR reactors, and also a reagent (3) which is used in the sensor are arranged. An analyte, the reagent (1) and the reagent (2) are injected through holes 108 and 109, respectively. The reagent may be freeze-dried, and dissolved by pouring a buffer solution when used. For a liquid transporting system of the second layer, a pump 110 and a valve 111 are arranged to pour the reagent to the first layer side and control the input to the PCR reactor and timing.

Figure 2:
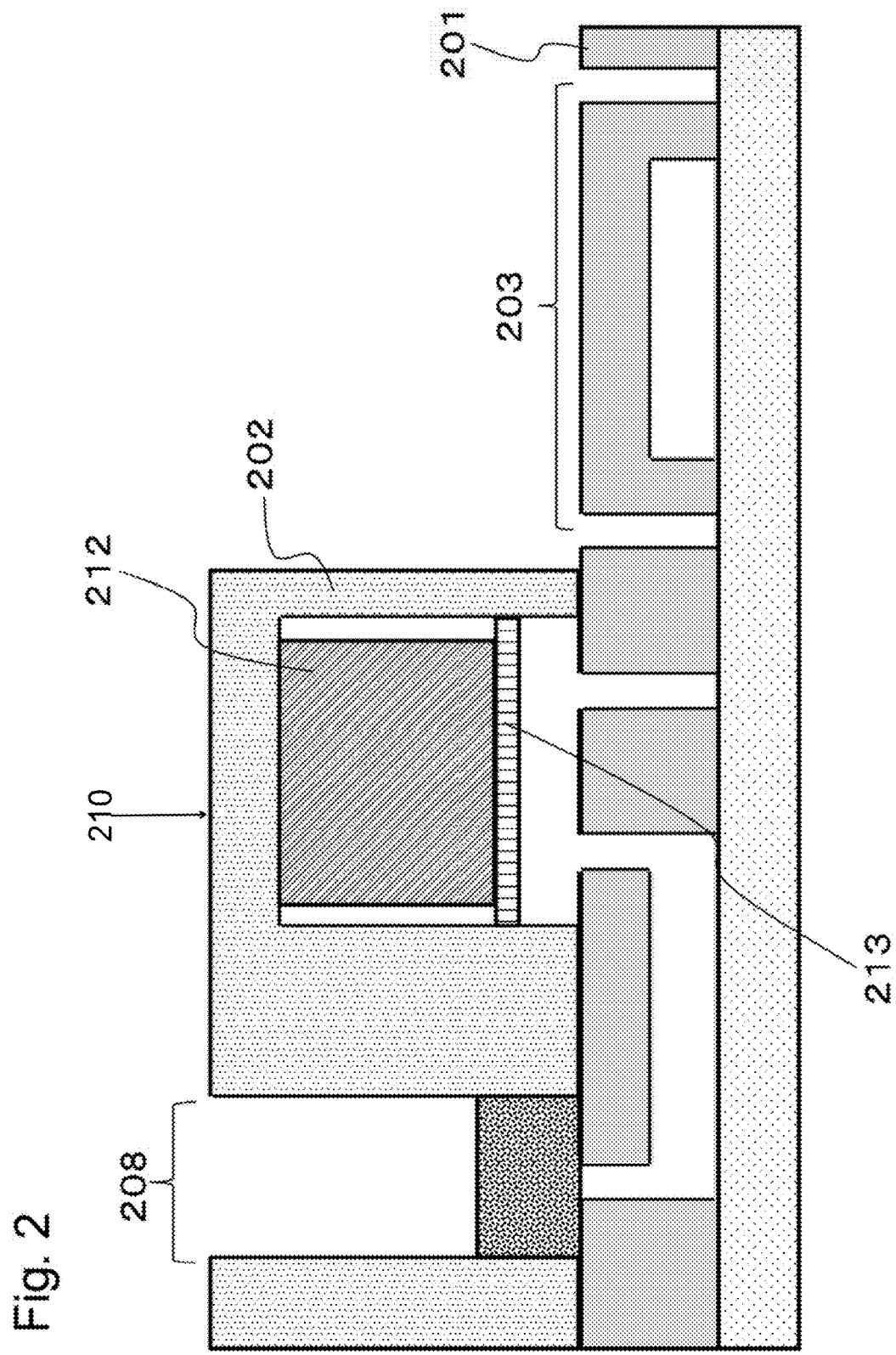
FIG. 2 is a sectional schematic view showing components of the DNA chip with micro-channel for DNA analysis according to the present disclosure.

FIG. 2 is sectional schematic view showing components of the DNA chip with micro-channel for DNA analysis according to the present disclosure. FIG. 2 is a sectional view including a reagent and a pump. A pump 210 is embedded in the second layer, and can be easily attached and detached. An actuator 212 of a driving section of the pump 210, for which a piezo element or a polymer actuator may be used, is arranged such that a membrane 213 can be driven. Given that the chip is disposable, for example, an inexpensive polymer actuator may be used. The first layer includes a micro-channel, which is patterned from the lower surface by photolithography and RIE (reactive ion gas etching). For tightly closing the patterned channel, a Pyrex glass 214 is used as a lid. The Pyrex glass 214 is bonded to the lower surface of the first layer using an anodic oxidation method. For connecting components included in the second layer and the micro-channel of the first layer, a through-hole is formed from the upper surface before the second layer is bonded. Further, as described above, the second layer is connected so as not to overlap a region where a PCR reactor 203 is arranged.

Figure 3:
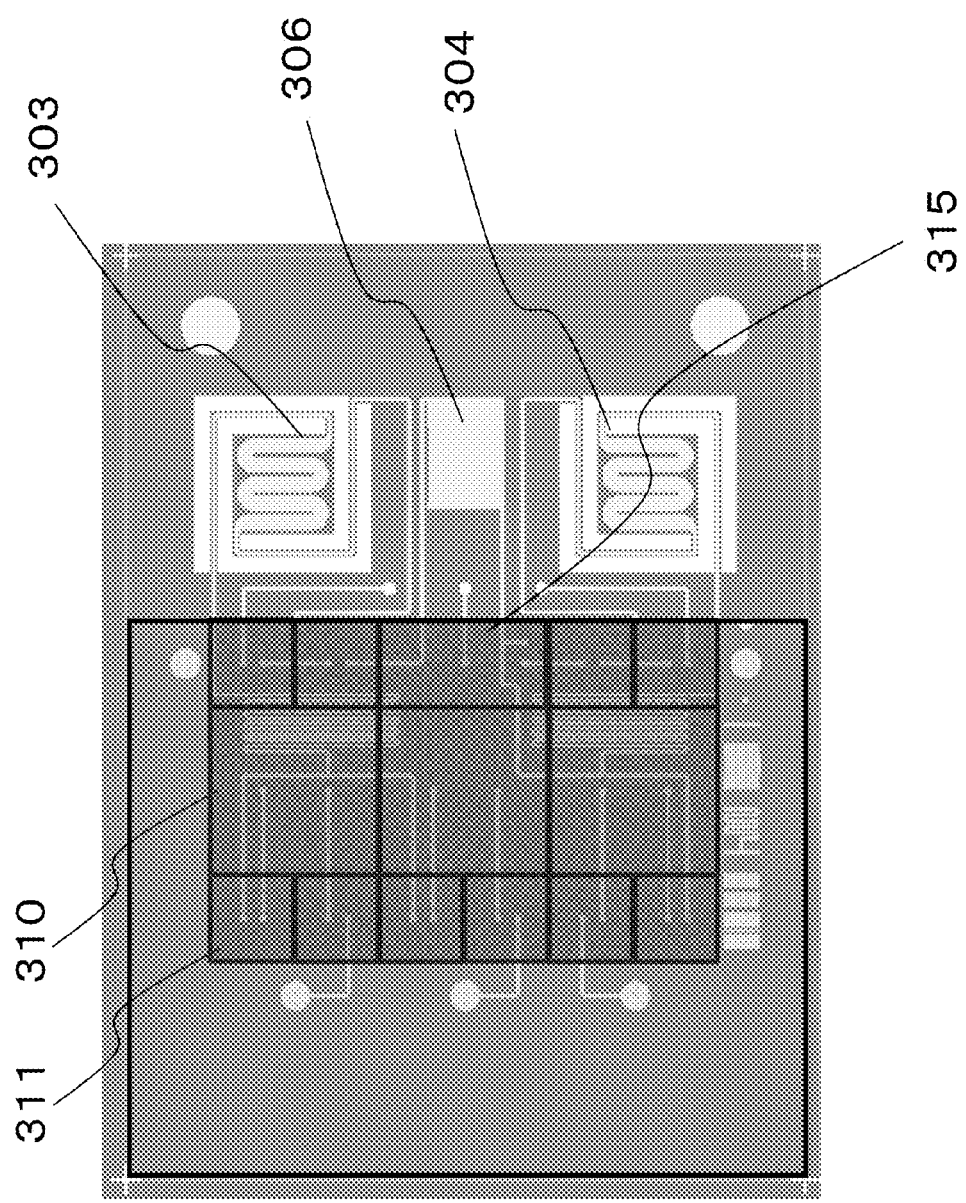
FIG. 3 is a layout view of components included in a silicon chip and a plastic section in the present disclosure.

FIG. 3 is a layout view of components included in first and second layers used in an embodiment of the present disclosure. The thickness of the first layer is, for example, about 500 to 800 μm. The parts are etched from the upper surface and the lower surface using two masks. The peripheries of a PCR reactor 1: 303 and a PCR reactor 2: 304 are mostly etched from both the upper and lower surfaces by RIE to be completely hollowed out, so that the PCRs are thermally isolated. On the other hand, a channel, a mixer 305 and a micro-sieve 306 are formed by etching the lower surface to a depth of about 300 μm by RIE, and a Pyrex glass is anodic oxidation-bonded to cover the surface. Through-holes of connection areas between holes 307, 308 and 309 and the second layer are formed by etching the upper surface to a depth of about 300 μm by RIE.

On the other hand, for components included in the second layer, a pump of a polymer actuator is mounted at the location of symbol 310, and a valve of the polymer actuator is mounted at the location of symbol 311. A sensor is mounted at the location of symbol 315.

Figure 4:
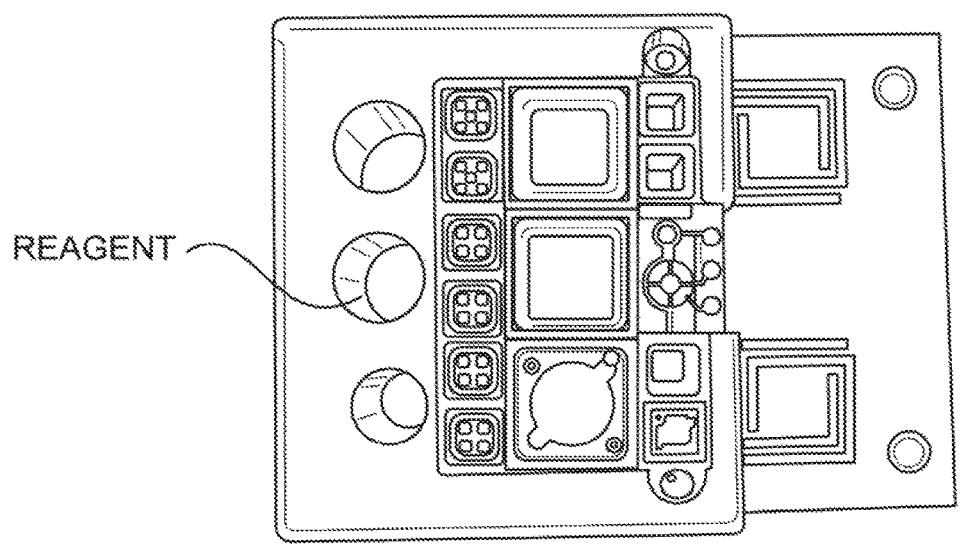
FIG. 4 is a chip with micro-channel which is obtained by using a method of the present disclosure.

FIG. 4 shows a photograph of the second layer and the first layer bonded thereto in a DNA chip with micro-channel for DNA analysis which is actually prepared in this embodiment.

EXAMPLE 1

Figure 5B:
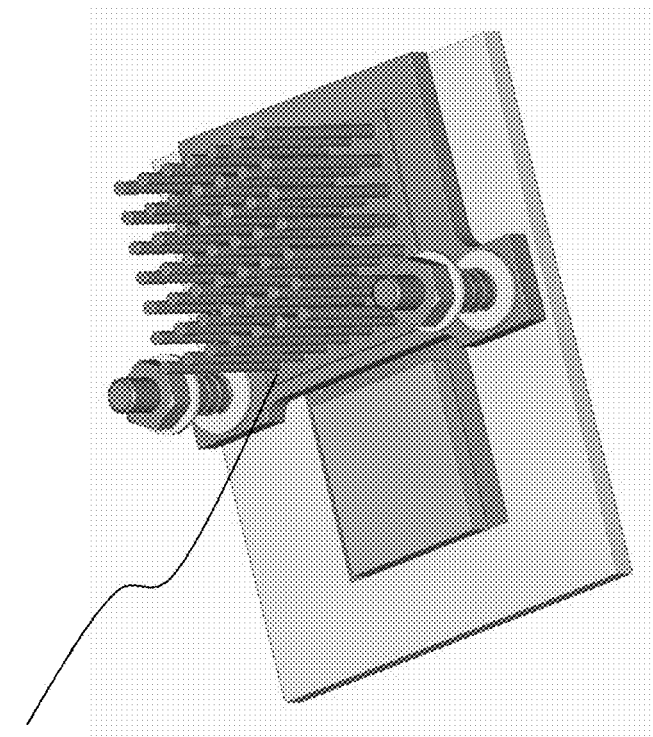
FIG. 5B is a schematic completion drawing showing connection of the chip with micro-channel in the present disclosure and a heat control system.
Figure 5A:
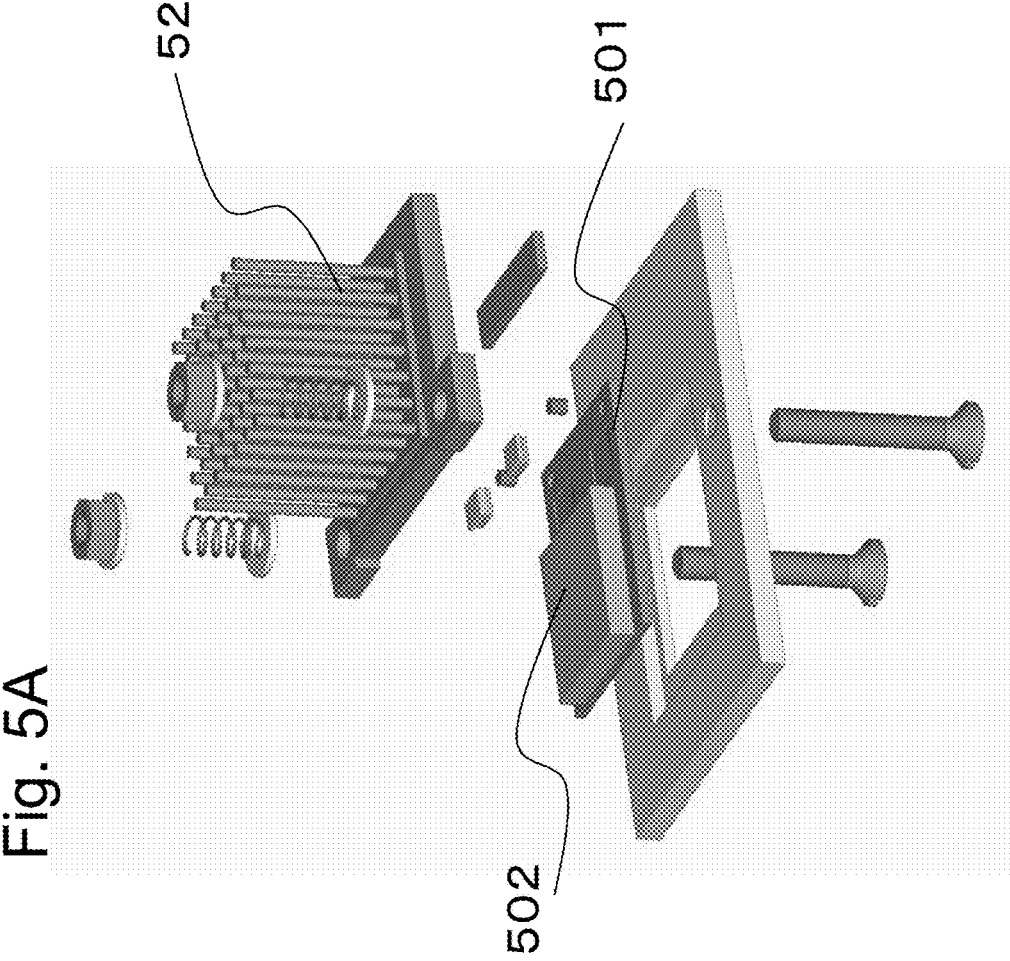
FIG. 5A is a schematic development view showing connection of the chip with micro-channel in the present disclosure and a heat control system.

FIGS. 5A and 5B are schematic views showing connection of a DNA chip with micro-channel for DNA analysis obtained in the present disclosure and a heat sink 521. The PCR reactors were arranged so as to gather on a side closer to the end of the first layer than the center of the first layer, and the silicon surface (upper surface) of the first layer including the PCR reactors was exposed without being covered with the second layer, so that a heat sink 521 having high efficiency and a large size could be attached to two PCRs.

Figure 6:
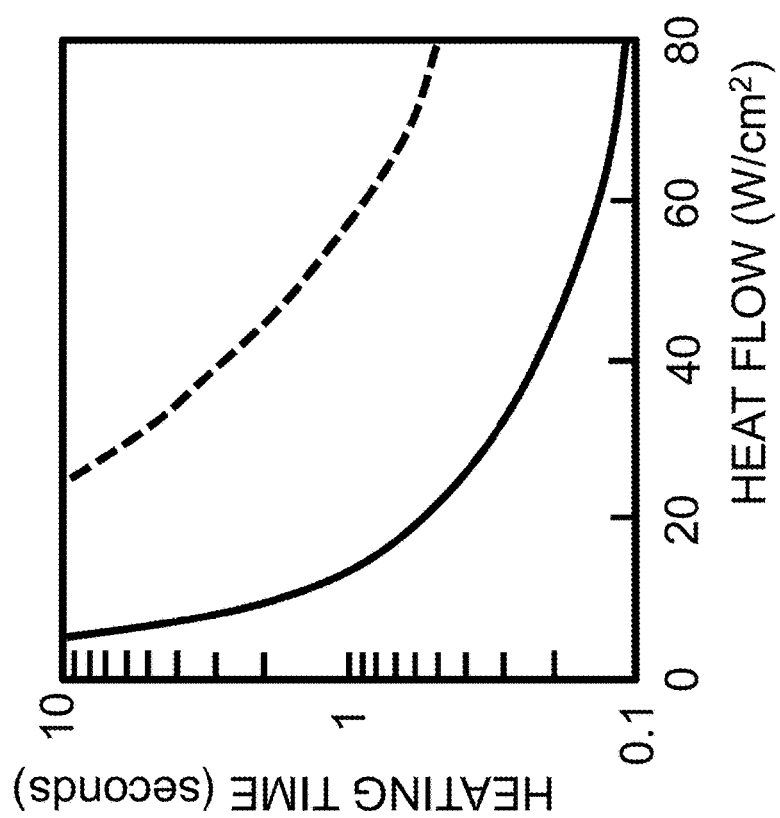
FIG. 6 is a graph showing a relation of a heating time to a heat flow in a PCR reactor, which is obtained in example 1 of the present disclosure.

As a result, a relation as in FIG. 6 could be obtained for a time taken for heating (or cooling) to an amount of heat supplied. In FIG. 6, the solid line corresponds to a curve obtained as described above, and the dotted line corresponds to a curve where a heat sink is absent. It was confirmed that the heating time was shortened at least by one-digit as shown in FIG. 6.

DNA was amplified from a human genome analyte by using a DNA chip with micro-channel for DNA analysis according to one embodiment of the present disclosure. As a model of DNA amplification, a human genome was used as a template. Control Primer 1 (5'-TAGGAAGGATGTC-CTCG-3': sequence 1) and Primer 3 (5'-TTCTTGATG-GCAAACACAGTTAAC-3': sequence 2) were used as primers for amplifying a DNA fragment from the sixth exon of a human genome.

Figure 7:
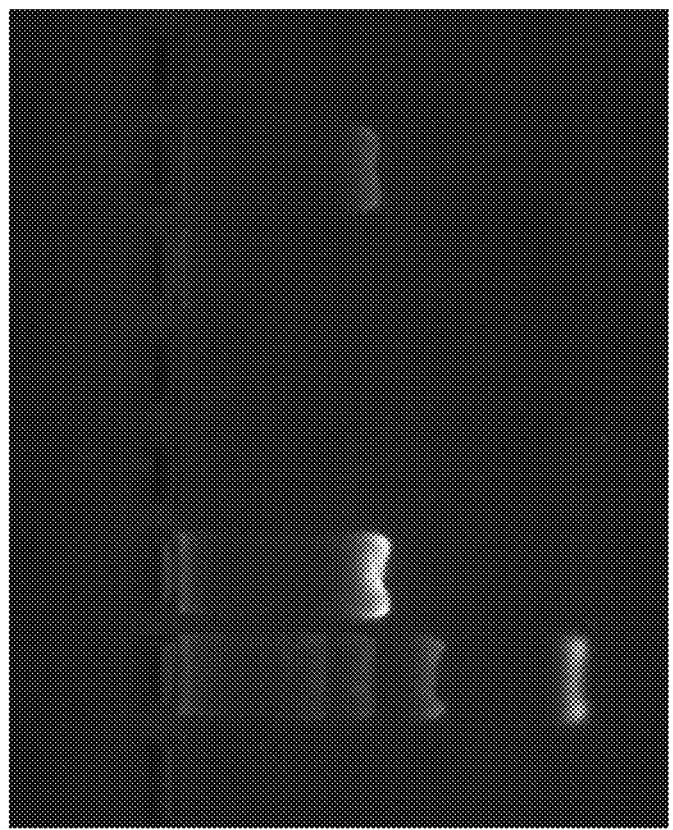
FIG. 7 shows a result of genetic analysis, which is obtained in example 2 of the present disclosure.

The reagent (A) a reagent 1 was mixed with an analyte in a mixer, and then reaction in a PCR 1 reactor was carried out in 35 cycles (45 minutes) of PCR under conditions of 98° C. for 30 seconds, 60° C. for 30 seconds and 68° C. for 30 seconds. Subsequently, impurities were removed with a micro-sieve. Three μL of this sample solution was collected, and existence or nonexistence of DNA amplification was checked by electrophoresis. The second lane in FIG. 7 corresponds to the result for existence or nonexistence of amplification of the DNA fragment collected from the sample. As shown in the lane 6 in FIG. 7, it was confirmed that a desired DNA fragment was amplified in only 45 minutes.

According to the present disclosure, there can be provided a DNA chip with micro-channel for DNA analysis, which is capable of performing extraction and amplification of DNA or detection of a sequence of the DNA quickly and conveniently, by enhancing heat dissipation performance of PCR to sufficiently improve the temperature increasing and decreasing speed of the PCR.

The invention claimed is:

1. A DNA chip with a micro-channel for DNA analysis of DNA included in an analyte according to a PCR method, the DNA chip comprising:
   a first layer made of silicon;
   a second layer made of plastic;
   a first channel;
   a second channel; and
   a third channel,
   wherein the second layer is formed on a partial area of the first layer, and
   the second layer comprises:
      a first pump;
      a second pump;
      a third pump;
      a hole configured to inject an analyte;
      a hole configured to inject a first reagent;
      a hole configured to inject a second reagent; and
      a sensor,
   the first layer includes a first PCR reactor and a second PCR reactor provided on an area on which the second layer is not formed, and
   the first channel is passed through the hole configured to inject the analyte, the first pump, the first PCR reactor, the second PCR reactor, and the sensor in sequence, and
   the second channel is passed through the hole configured to inject the first reagent and the second pump in sequence, and
   the third channel is passed through the hole configured to inject the second reagent and the third pump in sequence, and
   the second channel is provided on the first layer and the second channel is connected to the first channel between the first pump and the first PCR reactor, and
   the third channel is provided on the first layer and the third channel is connected to the first channel between the first PCR reactor and the second PCR reactor.

2. The DNA chip according to claim 1, wherein the PCR reactor is provided on an area closer to an end of the first layer than to the center of the first layer.

* * * * *

SEQUENCE LISTING

<160> NUMBER OF SEQ ID NOS: 2

<210> SEQ ID NO 1
<211> LENGTH: 17
<212> TYPE: DNA
<213> ORGANISM: Artificial Sequence
<220> FEATURE:
<223> OTHER INFORMATION: primer

<400> SEQUENCE: 1
taggaaggat gtcctcg                                                17

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
ttcttgatgg caaacacagt taac                                        24